(12) United States Patent
Libbus et al.

(10) Patent No.: US 8,452,401 B2
(45) Date of Patent: *May 28, 2013

(54) METHOD AND DEVICE FOR COMPREHENSIVE ANTI-TACHYARRHYTHMIA THERAPY

(75) Inventors: Imad Libbus, St. Paul, MN (US); Andrew P. Kramer, Marine on St. Croix, MN (US); William J. Linder, Golden Valley, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/287,842

(22) Filed: Nov. 2, 2011

(65) Prior Publication Data
US 2012/0046703 A1 Feb. 23, 2012

Related U.S. Application Data

(63) Continuation of application No. 11/122,968, filed on May 5, 2005, now Pat. No. 8,055,340.

(51) Int. Cl.
A61N 1/36 (2006.01)

(52) U.S. Cl.
USPC .......................... 607/14; 607/4; 607/5; 607/7

(58) Field of Classification Search
USPC ............................................... 607/4, 5, 7, 14
See application file for complete search history.

(56) References Cited

U.S. PATENT DOCUMENTS

| 5,203,326 | A | 4/1993 | Collins |
| 5,318,591 | A | 6/1994 | Causey, III et al. |
| 6,058,328 | A | 5/2000 | Levine et al. |
| 6,134,470 | A * | 10/2000 | Hartlaub ................. 607/14 |
| 6,400,986 | B1 * | 6/2002 | Sun et al. ................. 607/14 |
| 6,449,503 | B1 | 9/2002 | Hsu |
| 7,225,017 | B1 * | 5/2007 | Shelchuk ................. 607/4 |
| 8,055,340 | B2 * | 11/2011 | Libbus et al. ............ 607/14 |
| 2002/0058968 | A1 | 5/2002 | Sun et al. |
| 2002/0068875 | A1 | 6/2002 | Schroeppel et al. |
| 2002/0188215 | A1 | 12/2002 | Ferek-Petric |
| 2005/0197675 | A1 | 9/2005 | David et al. |
| 2006/0253157 | A1 | 11/2006 | Libbus et al. |
| 2007/0260283 | A1 * | 11/2007 | Li ........................ 607/4 |

FOREIGN PATENT DOCUMENTS

| EP | 0253505 A2 | 1/1988 |
| EP | 0547734 A2 | 6/1993 |
| EP | 0688577 A1 | 12/1995 |
| EP | 1640035 A1 | 3/2006 |

(Continued)

OTHER PUBLICATIONS

U.S. Appl. No. 11/122,968 Non-Final Office Action mailed Jul. 7, 2010, 8 pgs.

(Continued)

*Primary Examiner* — Joseph Stoklosa
(74) *Attorney, Agent, or Firm* — Schwegman Lundberg & Woessner, P.A.

(57) ABSTRACT

A method and apparatus for delivering therapy to treat ventricular tachyarrhythmias is described. In one embodiment, neural stimulation, anti-tachycardia pacing, and shock therapy are employed in a progressive sequence upon detection of a ventricular tachycardia.

20 Claims, 4 Drawing Sheets

FOREIGN PATENT DOCUMENTS

| | | | |
|---|---|---|---|
| JP | 838626 | A | 2/1996 |
| JP | 2004351122 | A | 12/2004 |
| JP | 2004536678 | A | 12/2004 |
| WO | WO-03011391 | A2 | 2/2003 |
| WO | WO-2004105870 | A1 | 12/2004 |
| WO | WO-2005030324 | A1 | 4/2005 |
| WO | WO-2006121836 | A1 | 11/2006 |

OTHER PUBLICATIONS

U.S. Appl. No. 11/122,968, Advisory Action mailed Oct. 14, 2008, 3 pgs.

U.S. Appl. No. 11/122,968, Final Office Action mailed Jun. 26, 2008, FOAR, 8 Pgs.

U.S. Appl. No. 11/122,968, Final Office Action mailed Aug. 6, 2009, 8 Pgs.

U.S. Appl. No. 11/122,968, Final Office Action mailed Dec. 9, 2010, 9 pgs.

U.S. Appl. No. 11/122,968, Non-Final Office Action mailed Dec. 11, 2007, OARN, 12 pgs.

U.S. Appl. No. 11/122,968, Non-Final Office Action mailed Dec. 28, 2009, 8 Pgs.

U.S. Appl. No. 11/122,968, Notice of Allowance mailed Aug. 19, 2011, 7 pgs.

U.S. Appl. No. 11/122,968, Office Action mailed Jan. 23, 2009, 8 pgs.

U.S. Appl. No. 11/122,968, Response filed Mar. 29, 2010 to Non Final Office Action mailed Dec. 28, 2009, 7 pgs.

U.S. Appl. No. 11/122,968, Response filed Oct. 7, 2010 to Non Final Office Action mailed Jul. 7, 2010, 8 pgs.

U.S. Appl. No. 11/122,968, Response filed Dec. 7, 2009 to Final Office Action mailed Aug. 6, 2009, 7 pgs.

U.S. Appl. No. 11/122,968, Response filed Mar. 11, 2008 to Non-Final Office Action mailed Dec. 11, 2007, 11 pgs.

U.S. Appl. No. 11/122,968, Response filed Apr. 22, 2009 to Non Final Office Action mailed Jan. 23, 2009, 9 pgs.

U.S. Appl. No. 11/122,968, Response filed Sep. 26, 2008 to Non-Final Office Action mailed Jun. 26, 2008, 10 pages.

European Application Serial No. 06752307.6, Office Action mailed Nov. 3, 2008, 4 pgs.

International Search Report and Written Opinion for Application No. PCT/US2006/017375, 12 Pages.

Chapleau, M W, "Neuro-cardiovascular regulation: from molecules to man. Introduction.", Annals of the New York Academy of Sciences, 940, (Jun. 2001), xiii-xxii.

Japanese Application Serial No. 2008-510246, Office Action mailed Nov. 7, 2011, (w/ English Translation), 7 pgs.

Japanese Application Serial No. 2008-510246, Response filed Feb. 7, 2012 to Office Action mailed Nov. 7, 2011, (w/ English Translation of Claims), 9 pgs.

* cited by examiner

METHOD AND DEVICE FOR COMPREHENSIVE ANTI-TACHYARRHYTHMIA THERAPY

CLAIM OF PRIORITY

This application is a continuation of and claims the benefit of priority under 35 U.S.C. §120 to U.S. patent application Ser. No. 11/122,968, filed on May 5, 2005, now issued as U.S. Pat. No. 8,055,340, which is hereby incorporated by reference herein in its entirety.

FIELD OF THE INVENTION

This invention pertains to methods and system for treating cardiac arrhythmias with electrical stimulation.

BACKGROUND

Tachyarrhythmias are abnormal heart rhythms characterized by a rapid heart rate. Examples of tachyarrhythmias include supraventricular tachycardias (SVT's) such as atrial tachycardia (AT), and atrial fibrillation (AF). The most dangerous tachyarrhythmias, however, are ventricular tachyarrhythmias: ventricular tachycardia (VT) and ventricular fibrillation (VF). Ventricular rhythms occur when re-entry of a depolarizing wavefront in areas of the ventricular myocardium with different conduction characteristics becomes self-sustaining or when an excitatory focus in the ventricle usurps control of the heart rate from the sinoatrial node. The result is rapid and ineffective contraction of the ventricles out of electromechanical synchrony with the atria. Most ventricular rhythms exhibit an abnormal QRS complex in an electrocardiogram because they do not use the normal ventricular conduction system, the depolarization spreading instead from the excitatory focus or point of re-entry directly into the myocardium. Ventricular tachycardia is typically characterized by distorted QRS complexes that occur at a rapid rate, while ventricular fibrillation is diagnosed when the ventricle depolarizes in a chaotic fashion with no identifiable QRS complexes. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion (an electrical shock delivered to the heart synchronously with the QRS complex to terminate VT or AF) and defibrillation (an electrical shock delivered without synchronization to the QRS complex to terminate VF) can be used to terminate most tachyarrhythmias. The electric shock terminates the tachyarrhythmia by depolarizing all of the myocardium simultaneously and rendering it refractory. A class of cardiac rhythm management devices known as an implantable cardioverter defibrillator (ICD) provides this kind of therapy by delivering a shock pulse to the heart when the device detects tachyarrhythmias.

Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICD's typically have ATP capability so that ATP therapy is delivered when VT is detected, while a shock pulse can be delivered to terminate both VT and VF. Although cardioversion/defibrillation will terminate ventricular tachycardia, it consumes a large amount of stored power from the battery and results in patient discomfort owing to the high voltage of the shock pulses. It is desirable, therefore, for the ICD to terminate a tachyarrhythmia whenever possible without using shock therapy. Devices have therefore been programmed to use cardioversion/defibrillation shocks to terminate fibrillation and certain high rate tachycardias and to use ATP to treat lower rate tachycardias.

SUMMARY

Described herein is a device and method for treating atrial or tachyarrhythmias which, in addition to ATP and shock therapy, employs neural stimulation. The neural stimulation may be parasympathetic stimulation or sympathetic inhibition. In an exemplary embodiment, a device is programmed to deliver the therapies in a tiered manner in response to detection of a tachyarrhythmia. The neural stimulation aids in terminating certain tachyarrhythmias without resort to shock therapy and can also be used in conjunction with shock therapy.

DETAILED DESCRIPTION

Cardiac rate, contractility, and excitability are known to be modulated by centrally mediated reflex pathways. Baroreceptors and chemoreceptors in the heart, great vessels, and lungs, transmit cardiac activity through vagal and sympathetic afferent fibers to the central nervous system. Activation of sympathetic afferents triggers reflex sympathetic activation, parasympathetic inhibition, vasoconstriction, and tachycardia. In contrast, parasympathetic activation results in bradycardia, vasodilation, and inhibition of vasopressin release. The present disclosure relates to an implantable device with the capability of sensing the presence of a tachyarrhythmia and terminating the arrhythmia with a combination of neural stimulation, ATP, and high-voltage shocks. Neural stimulation, in the form of sympathetic inhibition or parasympathetic activation, decreases myocardial excitability and conduction time to thereby increase the likelihood of arrhythmia termination. The neural stimulation thus improves the efficacy of ATP, and/or lowers defibrillation threshold for shock therapy. Described below is an exemplary device which may be configured to treat atrial and ventricular tachyarrhythmias with ATP, shock therapy, and neural stimulation. A particular implementation algorithm is also described.

1. Hardware Platform

Figure 1:
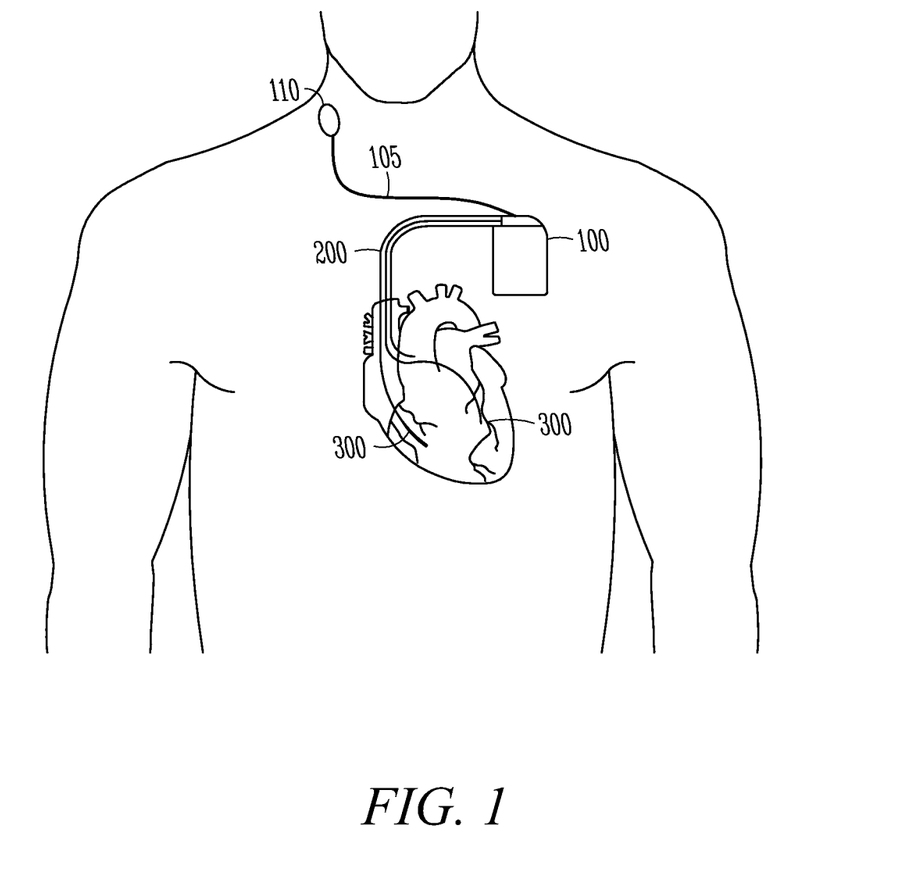
FIG. 1 illustrates the physical placement of an implantable cardiac device.

As shown in FIG. 1, an implantable cardiac device 100 for delivering tachyarrhythmia therapy is typically placed subcutaneously or submuscularly in a patient's chest with leads 200 threaded intravenously into the heart to connect the device to electrodes 300 used for sensing and pacing of the atria and/or ventricles. Electrodes may also be positioned on the epicardium by various means. A programmable electronic controller causes electrical stimulation for terminating a tachyarrhythmia to be output in response to sensed cardiac electrical activity. The device senses intrinsic cardiac electrical activity through a sensing channel which incorporates internal electrodes disposed near the chamber to be sensed. A depolarization wave associated with an intrinsic contraction of the atria or ventricles that is detected by the device is referred to as an atrial sense or ventricular sense, respectively, and the atrial and ventricular rates may be determined by measuring the intervals between senses. Also shown in the figure is a neural stimulation electrode 110 which may be a direct nerve cuff or a transvascular lead placed in, for example, the internal jugular vein for transvascular stimulation of the vagus nerve. The 110 electrode communicates with the device 100 via a lead 105 which passes subcutaneously from the device 100 to a point of venous access in the upper chest or neck.

Figure 2:
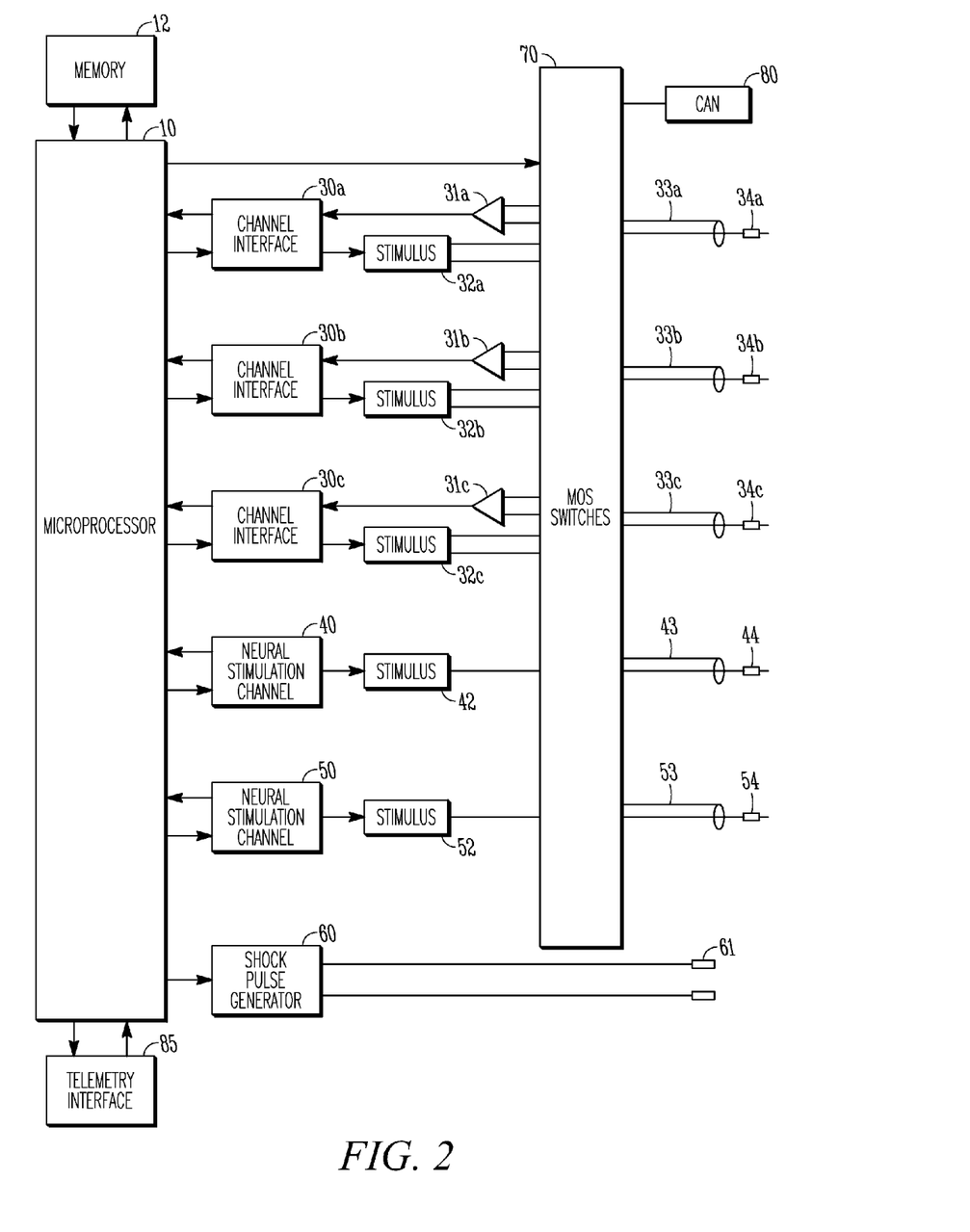
FIG. 2 is a block diagram of a cardiac rhythm management device with ATP, neuro-modulation and cardioversion/defibrillation capability.

FIG. 2 is a system diagram of a microprocessor-based cardiac rhythm management device with the capability of delivering cardioversion/defibrillation shocks, anti-tachycardia pacing therapy to either the ventricles or the atria, and neural stimulation. The controller of the device is a microprocessor 10 which communicates with a memory 12 via a bidirectional data bus. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor. Shown in the figure are three exemplary sensing and pacing channels designated "a" through "c" comprising bipolar leads with ring electrodes 33a-c and tip electrodes 34a-c, sensing amplifiers 31a-c, pulse generators 32a-c, and channel interfaces 30a-c. Each channel thus includes a pacing channel made up of the pulse generator connected to the electrode and a sensing channel made up of the sense amplifier connected to the electrode. The channel interfaces 30a-c communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a MOS switching network 70 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 80 or an electrode on another lead serving as a ground electrode. A shock pulse generator 60 is also interfaced to the controller for delivering a defibrillation shock via a pair of shock electrodes 61 to the atria or ventricles upon detection of a shockable tachyarrhythmia.

The controller may be programmed with a plurality of selectable ATP pacing protocols that define the manner in which anti-tachycardia pacing is delivered. In a microprocessor-based device, the output of pacing pulses is controlled by a pacing routine that implements the selected pacing protocol as defined by various parameters. A data structure stored in memory contains the parameter sets that define each of the available pacing protocols. Different protocols are apt to be more successful than others in terminating particular tachyarrhythmias that may differ as to rate and/or depolarization pattern. For this reason, modern cardiac rhythm management devices are capable of employing a number of different ATP protocols to deliver therapy.

Neural stimulation channels are incorporated into the device for delivering parasympathetic stimulation and/or sympathetic inhibition, where one channel includes a bipolar lead with a ring electrode 43 and a tip electrode 44, a pulse generator 42, and a channel interface 40, and the other channel includes a bipolar lead with a ring electrode 53 and a tip electrode 54, a pulse generator 52, and a channel interface 50. Other embodiments may use unipolar leads in which case the neural stimulation pulses are referenced to the can or another electrode. The pulse generator for each channel outputs a train of neural stimulation pulses which may be varied by the controller as to amplitude, frequency, and duty-cycle. In this embodiment, each of the neural stimulation channels uses a lead which can be intravascularly disposed near an appropriate stimulation site, e.g., near a baroreceptor in the case of a sympathetic inhibition channel or near a parasympathetic nerve in the case of a parasympathetic stimulation channel. Other types of leads and/or electrodes may also be employed. A nerve cuff electrode may be used in place of an intravascularly disposed electrode to provide neural stimulation, where the electrode may be placed, for example, around the cervical vagus nerve bundle to provide parasympathetic stimulation or around the aortic or carotid sinus nerve to provide sympathetic inhibition. In another embodiment, the leads of the neural stimulation electrodes are replaced by wireless links, and the electrodes for providing parasympathetic stimulation and/or sympathetic inhibition are incorporated into satellite units.

2. Exemplary Implementation

In an example embodiment, an implantable cardiac device with the capability of delivering ATP therapy, shock therapy, and neural stimulation such as illustrated by FIG. 2 is programmed to deliver the therapies in a tiered manner in response to detection of a tachyarrhythmia. The neural stimulation lead may be, for example, an expandable stimulation lead placed in the pulmonary artery in the proximity of a high concentration of baroreceptors, a transvascular lead placed proximal to one of the cardiac fat pads, an epicardial lead placed in the cardiac fat pad, or a cuff electrode placed around the aortic, carotid, or vagus nerve, or a transvascular lead placed proximal to one of these nerves. The device senses the presence of a tachyarrhythmia using conventional algorithms, and responds with a series of progressively more aggressive therapies. Such comprehensive anti-tachyarrhythmia therapy may be applied to atrial arrhythmias, ventricular arrhythmias, or both.

The device delivers anti-tachyarrhythmia therapy (i.e., ATP therapy, neural stimulation, and/or a defibrillation shock) under programmed control of the microprocessor in response to sensed activity from the sensing channels. A sensing routine analyzes the electrical activity received from the sensing channels in order to detect tachyarrhythmias. The ventricular rate is determined by measuring the time intervals between successive ventricular senses, referred to as RR intervals. A ventricular tachyarrhythmia is detected if the measured ventricular rate is above the tachycardia detection rate (TDR). Once a tachyarrhythmia is detected, the rhythm is classified as either tachycardia or fibrillation by comparing the heart rate to the fibrillation detection rate (FDR). Example values for the TDR and FDR would be 150 bpm and 200 bpm, respectively. If the ventricular rate is at or above the FDR, a life-threatening situation exists, and the device should be programmed to immediately deliver its most aggressive therapy. Thus, in the present embodiment, the device may be programmed to deliver shock therapy or a combination of shock therapy and neural stimulation without delay for tachyarrhythmias classified as fibrillation. For tachyarrhythmias below the FDR, however, the device may be programmed to deliver its different therapies in a progressive manner in an effort to avoid unnecessarily aggressive intervention. The device allows a physician to program one or more tiers for delivering the therapies, where each tier is programmed to contain one or more of the available therapies. In response to a tachyarrhythmia above the TDR but below the FDR, the therapies are then delivered in the tiered sequence until one is successful.

Figure 3:
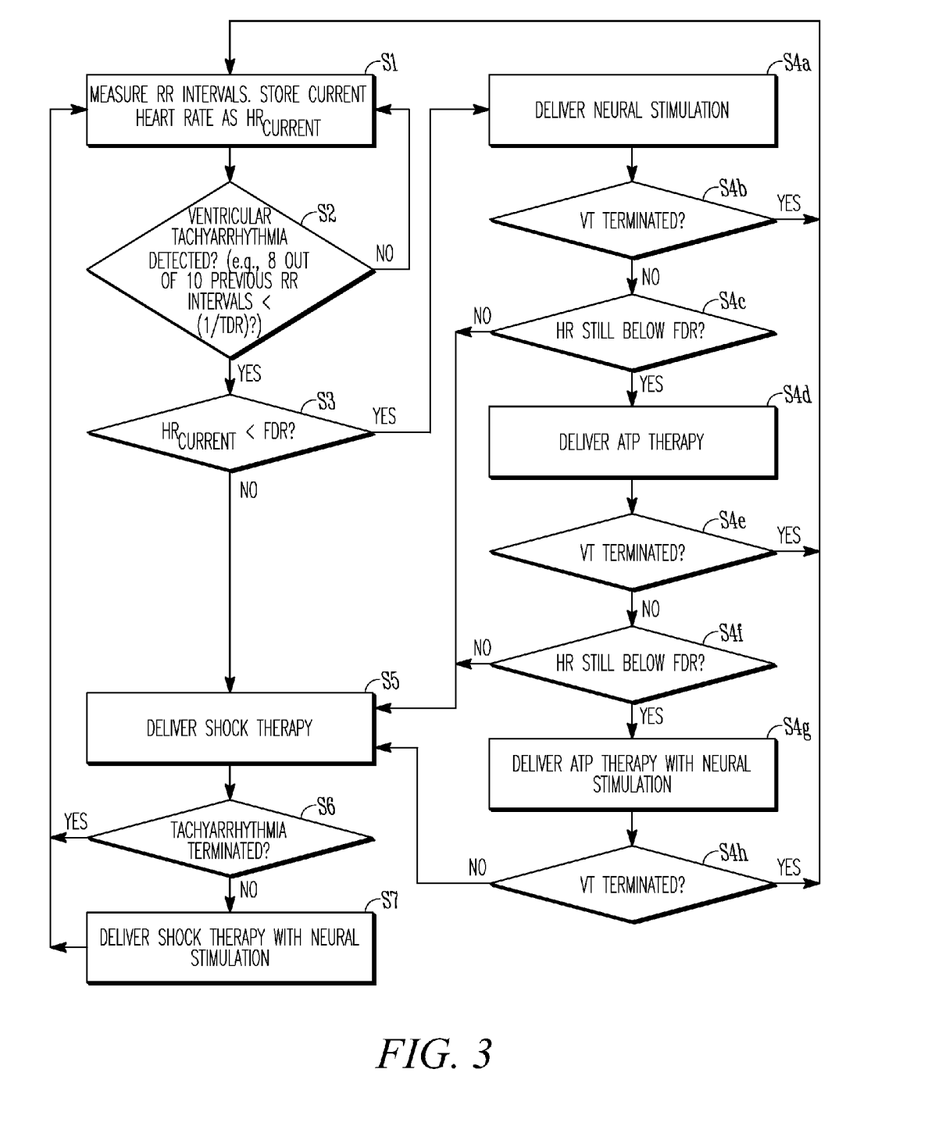
FIG. 3 is a flow diagram showing the therapy delivery steps performed in a particular embodiment.

In one embodiment, for example, the therapies are delivered in the following five-tiered sequence, where the sequence is stopped whenever the tachyarrhythmia is terminated:

1. Neural stimulation
2. Anti-tachycardia pacing
3. Neural stimulation+ATP
4. Shock therapy
5. Neural stimulation+shock therapy FIG. 3 is a flow diagram showing the steps performed by a cardiac rhythm management device in a particular algorithm for delivering neural stimulation, ATP therapy, and/or shock therapy to terminate a tachyarrhythmia using the approach described above. At step S1, the device measures RR intervals and stores the current heart rate as $HR_{current}$. The device determines whether a tachyarrhythmia is present by comparing the current heart rate with the TDR at step S2. If a tachyarrhythmia is detected (by, e.g., determining that 8 out of 10 previous RR intervals were fast or less than 60,000/TDR, where the RR intervals and the FDR are expressed in msecs and bpm, respectively.) and the current heart rate is above the FDR, the device proceeds to deliver shock therapy at step S5. If the tachyarrhythmia is still present as determined at step S6, the device next delivers shock therapy with neural stimulation at step S7 and returns to step S1. If the current heart rate is less than the FDR as determined at step S3, the tachyarrhythmia can be classified as a VT, and device starts a therapy sequence designated as steps S4a through S4h. At step S4a, neural stimulation is delivered. If steps S4b and S4c determine that the VT is still present and the heart rate is still below the FDR, ATP therapy is delivered at step S4d. If steps S4e and S4f determine that the VT has not been terminated and the heart rate is still below the FDR, ATP therapy with neural stimulation is delivered at step S4g. Step S4h then determines whether the VT has been terminated. If so, the device returns to step S1. If the VT is still present, the device proceeds with steps S5 through S7 as necessary to try to terminate the VT with shock therapy or shock therapy with neural stimulation. The device also proceeds with steps S5 through S7 if the heart rate is found to at or above the FDR at steps S4c and S4f during the therapy sequence.

The embodiment described with reference to FIG. 3 dealt with treating ventricular arrhythmias. A similar algorithm employing the same progressive therapy sequence could be executed by the device to treat atrial tachyarrhythmias. In that case, an atrial tachyarrhythmia would be detected by measuring the intervals between atrial senses, the TDR and FDR would be referenced to atrial rates, the ATP therapy would be atrial ATP, and the shock therapy would be cardioversion shocks designed to terminate AF. When a device is configured for delivering ventricular anti-tachycardia pacing or shocks in order to terminate ventricular tachycardias and for delivering atrial anti-tachycardia pacing or atrial conversion shocks in order to terminate atrial tachyarrhythmias, and it is important for the device to be able to distinguish between an SVT, which is an atrial tachyarrhythmia, and VT, which is a ventricular tachyarrhythmia. One way by which a device may distinguish between an SVT and VT is to employ a rate based test so that if a ventricular rate is detected that is high enough to constitute a VT, the arrhythmia is categorically classified as a VT if the ventricular rate is also greater than the atrial rate. A tachycardia in which the atrial rate is greater than or equal to the ventricular rate, on the other hand, may be a VT, an SVT, or a dual tachycardia where both VT and SVT are present simultaneously. Since VT is the more serious condition and requires prompt treatment, the rate based test may require that one or more additional rate based criteria be met before VT is ruled out. Such criteria, which help identify SVT, may include instability of the ventricular rate, lack of sudden onset, and an atrial rate above a specified atrial tachyarrhythmia threshold. Only if these one or more additional criteria are met is the tachycardia then classified as an SVT. The atrial tachyarrhythmia threshold may also be used to further classify the SVT as an atrial tachyarrhythmia requiring treatment, such as atrial fibrillation, or as ST which is not considered an arrhythmia and requires no treatment. In order to more accurately detect an SVT, a combined morphology/rate based test may be used instead of the rate based test described above for SVT/VT discrimination. In a combined morphology/rate based test, a morphology criterion based upon a morphology analysis of electrogram waveforms is used to provide an additional criterion for detecting an SVT. For example, SVT may be detected if: 1) the atrial rate is greater than or equal to the ventricular rate and, 2) some minimum number of ventricular beats are judged as normally conducted as determined by a morphology criterion involving morphology analyses of electrogram waveforms. An exemplary implementation of a morphology criterion for SVT/VT discrimination is disclosed in U.S. Pat. No. 6,449,503, assigned to Cardiac Pacemakers, Inc., the disclosure of which is hereby incorporated by reference in its entirety.

Figure 4:
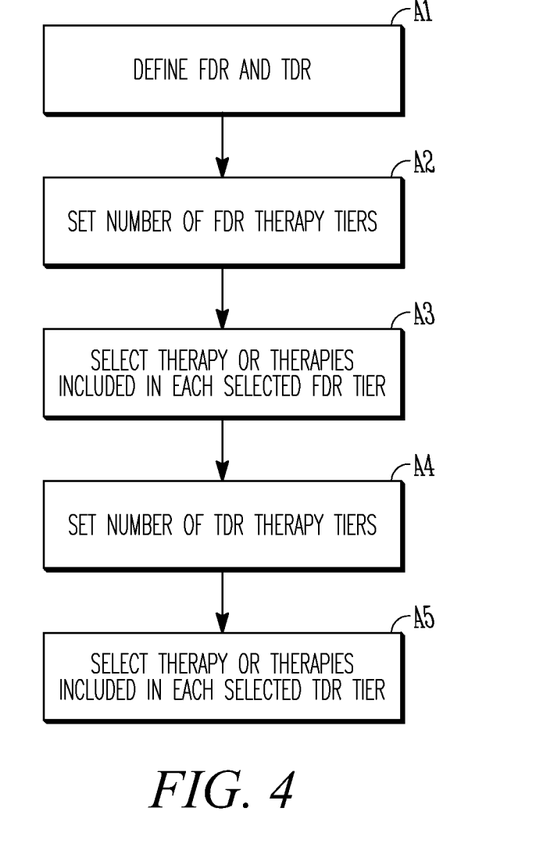
FIG. 4 is a flow diagram showing the configuration steps performed in a particular embodiment.

In one particular embodiment, the device is programmable with respect to the TDR, FDR, number of therapy tiers, and the particular therapy or therapies included within each tier. The device accepts user inputs via telemetry interface 85 (FIG. 2) to define a specified tachycardia detection rate (TDR) and a fibrillation detection rate (FDR), to define a number of TDR therapy tiers and select one or more therapies for inclusion in each TDR tier, to define a number of FDR therapy tiers and select one or more therapies for inclusion in each FDR tier. The one or more therapies which may be included in a TDR or FDR tier include neural stimulation, anti-tachycardia pacing (ATP) therapy, and shock therapy as well as possibly other types of tachyarrhythmia therapy such as drug delivery. Upon detection of a tachyarrhythmia, the device then delivers the therapies of the defined FDR tiers in a therapy sequence if the heart rate is above the FDR where the therapy sequence is stopped if the tachyarrhythmia is terminated. If the tachyarrhythmia is below the FDR, the device delivers the therapies of the defined TDR tiers in a therapy sequence wherein the therapy sequence is stopped if the tachyarrhythmia is terminated. FIG. 4 illustrates the steps a user would take in programming the device to treat tachyarrhythmias with comprehensive therapy. Such settings may be separately programmable for atrial and ventricular tachyarrhythmias. At step A1, the user defines the TDR and FDR. At step A2, the number of FDR therapy tiers used to treat tachyarrhythmias at or above the FDR are defined. At step A3, the particular therapy or therapies which are to be included in the defined FDR therapy tiers are selected. The number of TDR therapy tiers used to treat tachyarrhythmias between the TDR and the FDR are defined at step A4, and the therapy or therapies included in the each TDR tier is selected at step A5.

In another embodiment, the device may also be programmed such that the therapy sequence delivered upon detection of a tachyarrhythmia varies with the detected heart rate. For example, a plurality of heart rate ranges between the TDR and the FDR may be defined with a different therapy sequence for each such heart rate range. The number of heart rate ranges and the boundaries defining the ranges may be either programmable or fixed with the option of enabling the feature or not. For example, two heart rate ranges may be defined between the TDR and the FDR so that a VT is designated as either VT or FVT (fast VT). Separate therapy sequences could then be programmed for each type of VT. For example, the therapy sequence as described above starting with neural modulation alone could be used for VT, while the sequence would start with neural modulation together with ATP for FVT.

In another embodiment, device may be programmed to automatically alter the therapy sequence used to treat tachyarrhythmias in accordance with a recorded success/failure ratio for each therapy. In an exemplary implementation, the device records the successes and failures of each therapy in terminating tachyarrhythmias for a plurality of heart rate ranges between the TDR and the FDR and computes a success/failure ratio for each therapy at each heart rate range. If the success/failure ratio for a particular therapy at a particular heart rate range drops below a specified threshold value, or drops below a specified threshold difference from that of another therapy in the therapy sequence, then the unsuccessful therapy is discontinued from the therapy sequence for the particular heart rate range.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method for delivering anti-tachyarrhythmia therapy, comprising:
   generating an electrogram signal representing electrical activity in a cardiac chamber;
   detecting chamber senses and measuring a time interval between such senses to determine a current heart rate;
   detecting a tachyarrhythmia when the heart rate exceeds a specified tachycardia detection rate (TDR);
   upon detection of a tachyarrhythmia, delivering shock therapy if the heart rate is above a fibrillation detection rate (FDR);
   upon detection of a tachyarrhythmia below the FDR, delivering a sequence of different therapies where the sequence is stopped whenever the tachyarrhythmia is terminated;
   recording the successes and failures of each therapy of the sequence in terminating tachyarrhythmias for a plurality of heart rate ranges between the TDR and the FDR and computing a success/failure ratio for each therapy at each heart rate range; and,
   discontinuing a therapy from the sequence for a particular heart rate range if the success/failure ratio for a particular therapy at that particular heart rate range drops below a specified threshold value.

2. The method of claim 1 further comprising discontinuing a therapy from the sequence for a particular heart rate range if the success/failure ratio for a particular therapy at that particular heart rate range drops below a specified threshold difference from that of another therapy in the therapy sequence.

3. The method of claim 2 further comprising accepting an input defining the number of heart rate ranges and the boundaries defining the ranges.

4. The method of claim 1 wherein the sequence of different therapies include delivery of neural stimulation.

5. The method of claim 1 wherein the sequence of different therapies include delivery of anti-tachycardia pacing (ATP).

6. The method of claim 1 wherein the sequence of different therapies include delivery of neural stimulation and anti-tachycardia pacing ATP.

7. The method of claim 1 wherein the sequence of different therapies include delivery of shock therapy.

8. The method of claim 1 further comprising delivering neural stimulation with shock therapy if the heart rate is above the FDR.

9. The method of claim 1 wherein the cardiac chamber is a ventricle.

10. The method of claim 1 wherein the cardiac chamber is an atrium.

11. A cardiac device, comprising:
   a sensing amplifier for sensing an electrogram signal representing electrical activity in a cardiac chamber;
   a pulse generator for delivering anti-tachycardia pacing (ATP);
   a shock pulse generator for delivering shock therapy;
   a pulse generator for delivering neural stimulation that augments parasympathetic balance by parasympathetic stimulation or sympathetic inhibition;
   a controller, wherein the controller is programmed to:
   detect chamber senses and measure a time interval between such senses to determine a current heart rate;
   detect a tachyarrhythmia when the heart rate exceeds a specified tachycardia detection rate (TDR);
   upon detection of a tachyarrhythmia, deliver shock therapy if the heart rate is above a fibrillation detection rate (FDR);
   upon detection of a tachyarrhythmia below the FDR, deliver a sequence of different therapies where the sequence is stopped whenever the tachyarrhythmia is terminated;
   record the successes and failures of each therapy of the sequence in terminating tachyarrhythmias for a plurality of heart rate ranges between the TDR and the FDR and compute a success/failure ratio for each therapy at each heart rate range; and,
   discontinue a therapy from the sequence for a particular heart rate range if the success/failure ratio for a particular therapy at that particular heart rate range drops below a specified threshold value.

12. The device of claim 11 wherein the controller is further programmed to discontinue a therapy from the sequence for a particular heart rate range if the success/failure ratio for a particular therapy at that particular heart rate range drops below a specified threshold difference from that of another therapy in the therapy sequence.

13. The device of claim 12 wherein the controller is further programmed to accept an input defining the number of heart rate ranges and the boundaries defining the ranges.

14. The device of claim 11 wherein the sequence of different therapies include delivery of neural stimulation.

15. The device of claim 11 wherein the sequence of different therapies include delivery of anti-tachycardia pacing (ATP).

16. The device of claim 11 wherein the sequence of different therapies include delivery of neural stimulation and anti-tachycardia pacing ATP.

17. The device of claim 11 wherein the sequence of different therapies include delivery of shock therapy.

18. The device of claim 11 wherein the controller is further programmed to deliver neural stimulation with shock therapy if the heart rate is above the FDR.

19. The device of claim 11 wherein the cardiac chamber is a ventricle.

20. The device of claim 11 wherein the cardiac chamber is an atrium.

* * * * *